(12) United States Patent
Ainsworth et al.

(10) Patent No.: US 6,929,660 B1
(45) Date of Patent: Aug. 16, 2005

(54) INTRAVASCULAR STENT

(75) Inventors: Stephen D. Ainsworth, Los Gatos, CA (US); E Tina Cheng, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/746,746

(22) Filed: Dec. 22, 2000

(51) Int. Cl.[7] .................................................. A61F 2/06
(52) U.S. Cl. ...................................................... 623/1.15
(58) Field of Search ................................ 623/1.15, 1.1, 623/1.2, 1.16, 1.18, 1.19; 606/191, 194, 108, 195

(56) References Cited

U.S. PATENT DOCUMENTS

| | | | |
|---|---|---|---|
| 4,580,568 A | 4/1986 | Gianturco | |
| 4,827,321 A | 5/1989 | Roubin et al. | |
| 5,102,417 A | 4/1992 | Palmaz | |
| 5,104,404 A | 4/1992 | Wolff | |
| 5,292,331 A | 3/1994 | Boneau | |
| 5,499,373 A | 3/1996 | Pinchasik et al. | |
| 5,591,197 A | * 1/1997 | Orth et al. ................... | 606/194 |
| 5,607,442 A | 3/1997 | Fischell et al. | |
| 5,632,771 A | 5/1997 | Boatman et al. | |
| 5,643,312 A | 7/1997 | Fischell et al. | |
| 5,669,932 A | 9/1997 | Fischell et al. | |
| 5,674,241 A | 10/1997 | Bley et al. | |
| 5,674,278 A | 10/1997 | Boneau | |
| 5,697,971 A | * 12/1997 | Fischell et al. ............. | 623/1.15 |
| 5,733,303 A | 3/1998 | Israel et al. | |
| 5,741,327 A | 4/1998 | Frantzen | |
| 5,755,781 A | 5/1998 | Jayaraman | |
| 5,776,161 A | 7/1998 | Globerman | |
| 5,807,404 A | 9/1998 | Richter | |
| 5,810,872 A | 9/1998 | Kanesaka et al. | |
| 5,824,040 A | 10/1998 | Cox et al. | |

(Continued)

FOREIGN PATENT DOCUMENTS

| | | | |
|---|---|---|---|
| DE | 297 08879 U1 | 9/1997 | |
| EP | 0 088 093 B1 | 1/1986 | |
| EP | 0 372 789 A3 | 6/1990 | |
| EP | 0 806 190 A1 | 11/1997 | |
| EP | 806190 A1 * | 11/1997 | ............. A61F/2/06 |
| EP | 0 888 757 A1 | 1/1999 | |
| WO | WO 95/03010 | 2/1995 | |
| WO | WO 9732543 A1 * | 9/1997 | ............. A61F/2/06 |
| WO | WO 97/32544 | 9/1997 | |
| WO | WO 98/22159 | 5/1998 | |
| WO | WO 99/17680 | 4/1999 | |
| WO | WO 99/62430 | 12/1999 | |
| WO | WO 00/42945 | 7/2000 | |
| WO | WO 00/42946 | 7/2000 | |
| WO | WO 00/62710 | 10/2000 | |

*Primary Examiner*—Anhtuan T. Nguyen
*Assistant Examiner*—Jessica R. Baxter
(74) *Attorney, Agent, or Firm*—Fulwider Patton Lee & Utecht, LLP (57) ABSTRACT

The invention is directed to an expandable stent for implanting in a body lumen, such as a coronary artery, peripheral artery, or other body lumen. The invention provides for an intravascular stent having a plurality of cylindrical rings connected by links with apertures and/or undulating links. The apertured links and undulating links provide the stent with a high degree of flexibility in the longitudinal direction, yet the stent has adequate vessel wall coverage and radial strength sufficient to hold open an artery or other body lumen.

36 Claims, 7 Drawing Sheets

U.S. PATENT DOCUMENTS

| | | | |
|---|---|---|---|
| 5,836,964 A | | 11/1998 | Richter et al. |
| 5,843,120 A | | 12/1998 | Israel et al. |
| 5,843,168 A | | 12/1998 | Dang |
| 5,843,175 A | * | 12/1998 | Frantzen ............... 623/1.15 |
| 5,853,419 A | | 12/1998 | Imran |
| 5,868,781 A | | 2/1999 | Killion |
| 5,868,783 A | | 2/1999 | Tower |
| 5,876,449 A | | 3/1999 | Starck et al. |
| 5,879,370 A | | 3/1999 | Fischell et al. |
| 5,879,382 A | | 3/1999 | Boneau |
| 5,893,887 A | | 4/1999 | Jayaraman |
| 5,911,754 A | | 6/1999 | Kanesaka et al. |
| 5,913,895 A | | 6/1999 | Burpec et al. |
| 5,922,005 A | | 7/1999 | Richter et al. |
| 5,922,020 A | | 7/1999 | Klein et al. |
| 5,925,061 A | * | 7/1999 | Ogi et al. ............... 623/1.2 |
| 5,931,866 A | | 8/1999 | Frantzen |
| 5,935,162 A | | 8/1999 | Dang |
| 5,938,682 A | | 8/1999 | Hojeibane et al. |
| 5,938,697 A | | 8/1999 | Killion et al. |
| 5,948,016 A | | 9/1999 | Jang |
| 5,954,743 A | | 9/1999 | Jang |
| 5,964,798 A | | 10/1999 | Imran |
| 5,967,986 A | | 10/1999 | Cimochowski et al. |
| 5,968,093 A | | 10/1999 | Kranz |
| 5,972,018 A | | 10/1999 | Israel |
| 5,980,552 A | | 11/1999 | Pinchasik et al. |
| 5,993,489 A | | 11/1999 | Lewis et al. |
| 6,001,125 A | | 12/1999 | Golds et al. |
| 6,004,348 A | | 12/1999 | Banas et al. |
| 6,013,091 A | * | 1/2000 | Ley et al. ............... 623/1.16 |
| 6,017,365 A | | 1/2000 | Von Oepen |
| 6,019,789 A | | 2/2000 | Dinh et al. |
| 6,022,371 A | | 2/2000 | Killion |
| 6,022,374 A | | 2/2000 | Imran |
| 6,033,433 A | * | 3/2000 | Ehr et al. ............... 623/1.16 |
| 6,033,435 A | | 3/2000 | Penn et al. |
| 6,039,755 A | | 3/2000 | Edwin et al. |
| 6,039,756 A | | 3/2000 | Jang |
| 6,042,597 A | | 3/2000 | Kveen et al. |
| 6,042,606 A | | 3/2000 | Frantzen et al. |
| 6,048,361 A | | 4/2000 | Von Oepen |
| 6,051,020 A | | 4/2000 | Goicoechea et al. |
| 6,053,940 A | | 4/2000 | Wijay |
| 6,053,941 A | | 4/2000 | Lindenberg et al. |
| 6,053,943 A | | 4/2000 | Edwin et al. |
| 6,056,775 A | | 5/2000 | Borghi et al. |
| 6,056,776 A | | 5/2000 | Lau et al. |
| 6,059,822 A | | 5/2000 | Kanesaka et al. |
| 6,063,113 A | | 5/2000 | Kvteladze et al. |
| 6,066,168 A | | 5/2000 | Lau et al. |
| 6,066,169 A | | 5/2000 | McGuinness |
| 6,068,656 A | | 5/2000 | Von Oepen |
| 6,071,298 A | | 6/2000 | Lashinski et al. |
| 6,077,297 A | | 6/2000 | Robinson et al. |
| 6,080,191 A | | 6/2000 | Summers |
| 6,083,259 A | | 7/2000 | Frantzen |
| 6,086,604 A | | 7/2000 | Fischell et al. |
| 6,086,611 A | | 7/2000 | Duffy et al. |
| 6,090,127 A | | 7/2000 | Globerman |
| 6,093,199 A | | 7/2000 | Brown et al. |
| 6,093,203 A | | 7/2000 | Unflacker |
| 6,099,455 A | | 8/2000 | Columbo et al. |
| 6,099,559 A | | 8/2000 | Nolting |
| 6,099,560 A | | 8/2000 | Penn et al. |
| 6,099,561 A | | 8/2000 | Alt |
| 6,102,940 A | | 8/2000 | Robichon et al. |
| 6,106,548 A | | 8/2000 | Roubin et al. |
| 6,113,627 A | | 9/2000 | Jang |
| 6,113,628 A | | 9/2000 | Borghi |
| 6,117,165 A | | 9/2000 | Becker |
| 6,123,721 A | | 9/2000 | Jang |
| 6,129,754 A | | 10/2000 | Kanesaka et al. |
| 6,129,755 A | | 10/2000 | Mathis et al. |
| 6,152,957 A | | 11/2000 | Jang |
| 6,156,052 A | | 12/2000 | Richter |
| 6,162,243 A | | 12/2000 | Gray et al. |
| 6,179,868 B1 | | 1/2001 | Burpee et al. |
| 6,183,506 B1 | | 2/2001 | Penn et al. |
| 6,187,034 B1 | | 2/2001 | Frantzen |
| 6,190,403 B1 | | 2/2001 | Fischell et al. |
| 6,200,334 B1 | | 3/2001 | Jang |
| 6,200,337 B1 | * | 3/2001 | Moriuchi et al. ............ 623/1.16 |
| 6,206,916 B1 | | 3/2001 | Furst |
| 6,217,608 B1 | | 4/2001 | Penn et al. |
| 6,241,762 B1 | | 6/2001 | Shanley |
| 6,258,116 B1 | | 7/2001 | Hojeibane |
| 6,325,821 B1 | * | 12/2001 | Gaschino et al. ............ 606/194 |
| 6,652,573 B2 | * | 11/2003 | von Oepen ............... 623/1.15 |
| 2002/0151959 A1 | * | 10/2002 | von Oepen ............... 623/1.15 |

* cited by examiner

INTRAVASCULAR STENT

BACKGROUND OF THE INVENTION

This invention relates to vascular repair devices, and in particular intravascular stents, which are adapted to be implanted into a patient's body lumen, such as a blood vessel or coronary artery, to maintain the lumen's patency. Stents are particularly useful in the treatment of atherosclerotic stenosis in various blood vessels, and are most frequently used in connection with coronary angioplasty.

Stents are generally cylindrical devices which hold open a segment of blood vessel or other body lumen. They also are suitable to support and hold back a dissected arterial lining that can occlude the lumen. At present, numerous commercial stents are marketed throughout the world. While some of these stents are flexible and have the appropriate strength rigidity needed to hold open a lumen, such as a coronary artery, each stent design typically represents a compromise between the stent's flexibility and its radial strength. What has been needed, and heretofore unavailable, is a stent which has a high degree of flexibility so that it can be advanced through tortuous lumen and readily expanded, and yet have the mechanical strength to hold open the lumen or artery into which it is implanted and provide adequate vessel wall coverage. The present invention satisfies this need. That is, the stent of the present invention has a high degree of flexibility, making it possible to advance the stent easily through tortuous body passageways, yet the stent has sufficient radial strength so that it can hold open that lumen or passageway or tack up a dissected lining and still provide adequate vessel wall coverage.

SUMMARY OF THE INVENTION

The present invention is directed to an intravascular stent which is highly flexible along its longitudinal axis to facilitate delivery through tortuous body lumens, but which is strong and stable enough radially in its expanded condition to maintain the patency of a body lumen when the stent is implanted therein.

The stent of the present invention generally includes a plurality of cylindrical elements that are interconnected to form the stent. The stent typically is mounted on a balloon catheter if it is balloon expandable, or else it is mounted on a catheter without a balloon if it is self-expanding.

Each of the cylindrical rings or elements making up the stent has a proximal end and a distal end and a cylindrical plane defined by a cylindrical outer wall surface that extends circumferentially between the proximal end and the distal end of the cylindrical ring. In the preferred embodiment, cylindrical rings are interconnected by at least one flexible link which attaches one cylindrical ring to an adjacent cylindrical ring. The links allow the stent to be highly flexible along its longitudinal axis. The flexible links are positioned substantially within the cylindrical plane of the outer wall surface of the cylindrical rings. The design of these highly flexible interconnecting members provide for uniform scaffolding and a high percentage of vessel wall coverage.

The flexible links may take various configurations. One such configuration is an undulating or serpentine shape. The undulating links can include bends connected by substantially straight portions wherein the substantially straight portions are substantially perpendicular to the stent's longitudinal axis. Another configuration places one or more apertures, such as an oval, rectangle, or dog bone shape, in a generally straight link. The apertures are typically longer in one direction than another, with the longer direction oriented generally perpendicular to the longitudinal axis of the stent. Yet another form of the invention includes a link with an aperture and an undulating link portion.

In the case of the undulating links that interconnect the cylindrical rings, the positioning of the unexpanded links also enhances the flexibility by allowing uniform flexibility when the stent is bent in any direction along its longitudinal axis. Further, the cylindrical rings are configured to provide flexibility to the stent in that portions of the rings can flex or bend and tip out of the stent's cylindrical plane as the stent is delivered through a tortuous vessel.

The cylindrical rings typically are formed of a plurality of peaks and valleys, where the valleys of one cylindrical ring are circumferentially offset from the valleys of an adjacent cylindrical ring. In this configuration, at least one flexible link attaches each cylindrical ring to an adjacent cylindrical ring. Each undulating flexible link is positioned substantially within one of the valleys and it attaches the valley to an adjacent peak. The flexible links with the apertures may be positioned in or out of the valleys.

In one embodiment, the cylindrical rings and flexible links are not separate structures, although they have been conveniently referred to as rings and links for ease of identification. Further, the cylindrical rings can be thought of as comprising a series of U-shaped, W-shaped and Y-shaped structures in a repeating pattern. Again, while the cylindrical rings preferably are not manufactured as discrete U's, W's and Y's, the pattern of the cylindrical rings resemble such a configuration. The U's, W's and Y's promote flexibility in the stent primarily by at least some of them flexing and by tipping radially out of the stent's cylindrical plane as the stent is delivered through a tortuous vessel.

The undulating links are positioned so that the undulating portion is within the center peak (or valley) of the W-shaped portion, which generally increases the amount of vessel wall coverage. Since the undulating portion does not substantially expand (if at all) when the stent is expanded, it will continue to provide good vessel wall coverage even as the W-shaped portion spreads apart as the stent is expanded. The same is true for flexible links that incorporate apertures.

Typically, a balloon expandable stent is made from a stainless steel alloy or similar material. The cylindrical rings of the stent are plastically deformed when expanded by the balloon.

The cylindrical rings of the stent can expand radially outwardly without a balloon when the stent is formed from a superelastic alloy, such as nickel titanium (NiTi) alloys. These so-called "self-expanding" stents expand upon application of a temperature change or when a stress is relieved, as in the case of a pseudo-elastic phase change.

The number and location of flexible links that interconnect adjacent cylindrical rings can be varied as the application requires. Since the undulating portion of the flexible links typically do not expand when the cylindrical rings of the stent expand radially outwardly, the links continue to provide flexibility and to also provide a scaffolding function to assist in holding open the artery. Importantly, the addition or removal of the flexible links has very little impact on the overall longitudinal flexibility of the stent. Each flexible link is configured so that it promotes flexibility whereas prior art links typically reduce flexibility of the stent.

The links of the present invention provide the stent with a high degree of flexibility along the stent axis, which reduces the tendency of stent fishscaling. Stent fishscaling can occur when the stent is bent and portions of the stent project outward when the stent is in the unexpanded condition. The flexible links of the present invention reduce the likelihood of fishscaling.

Further, because of the positioning of the links, and the fact that the links do not expand or stretch when the stent is radially expanded, the overall length of the stent is substantially the same in the unexpanded and expanded configurations. In other words, the stent will not appreciably shorten upon expansion.

The stent is formed from a tube by laser cutting the pattern of cylindrical rings and flexible links in the tube. The stent also may be formed by laser cutting a flat metal sheet in the pattern of the cylindrical rings and links, and then rolling the pattern into the shape of the tubular stent and providing a longitudinal weld to form the stent.

DETAILED DESCRIPTION OF THE PREFERRED EMBODIMENTS

The present invention improves on existing stents by providing a longitudinally flexible stent having a uniquely designed pattern and novel interconnecting members. In addition to providing longitudinal flexibility, the stent of the present invention also provides radial strength and a high degree of scaffolding of a vessel wall, such as a coronary artery. The design of the highly flexible interconnecting members and their placement provides for uniform scaffolding and a high degree of vessel wall coverage.

Figures 1, 2, 3:
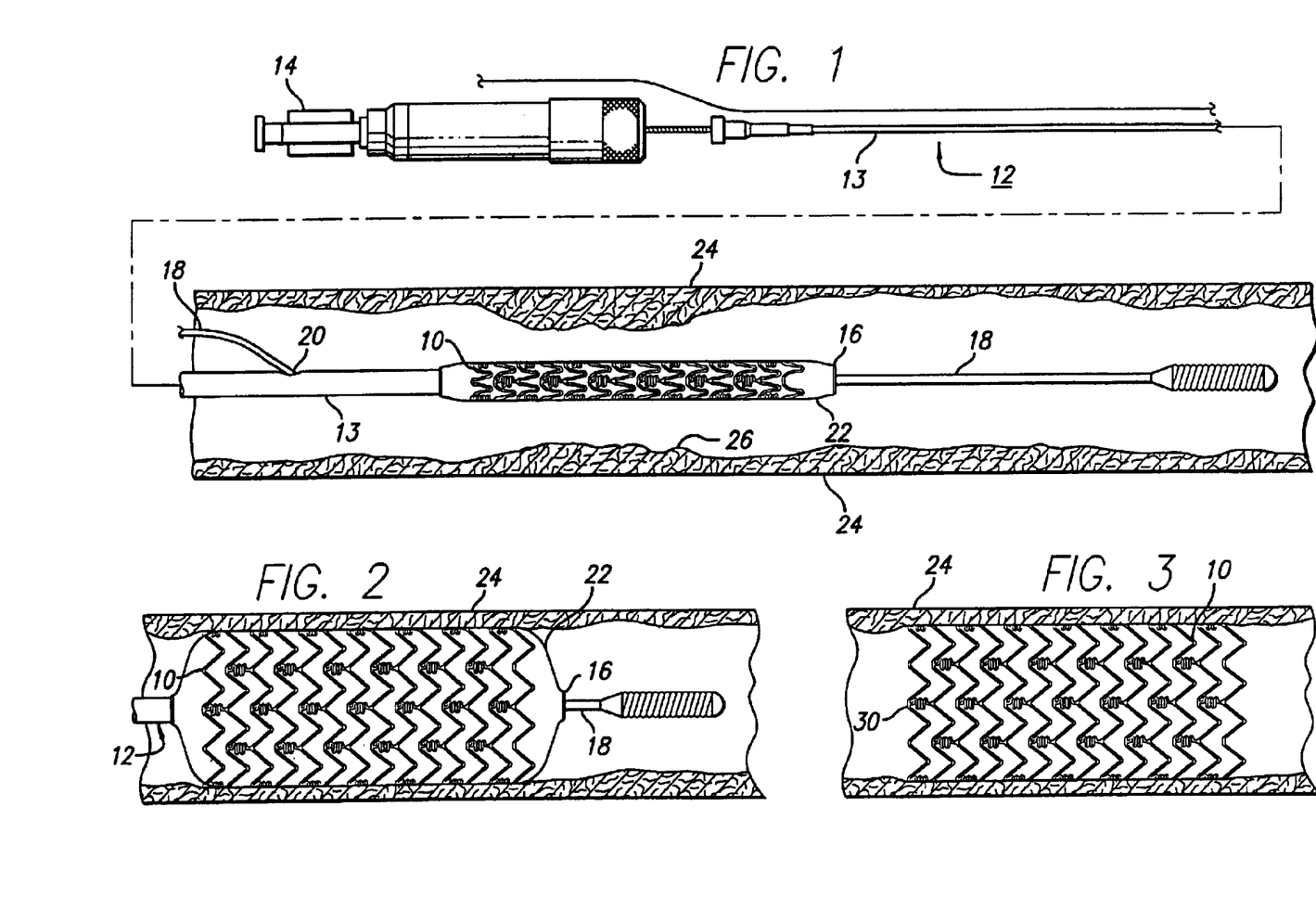
FIG. 1 is an elevation view, partially in section, of a stent which is mounted on a rapid-exchange delivery catheter and positioned within an artery.
FIG. 2 is an elevation view, partially in section, similar to that shown in FIG. 1, wherein the stent is expanded within the artery so that the stent embeds within the arterial wall.
FIG. 3 is an elevation view, partially in section, showing the expanded tent implanted within the artery after withdrawal of the rapid-exchange delivery catheter.

Turning to the drawings, FIG. 1 depicts the present invention stent 10 mounted on a catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over-the-wire system (not shown) or a well known rapid exchange catheter system, such as the one shown in FIG. 1.

Catheter assembly 12 as depicted in FIG. 1 includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 is used to repair a diseased or damaged arterial wall as shown in FIG. 1, or a dissection, or a flap which are commonly found in the coronary arteries and other blood vessels.

In a typical procedure to implant stent 10, the guide wire 18 is advanced through the patient's vascular system by well known methods so that the distal end of the guide wire is advanced past the plaque or diseased area 26. Prior to implanting the stent, the cardiologist may wish to perform an angioplasty or other procedure (i.e., atherectomy) in order to open and remodel the vessel and the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in. FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 holds open the artery after the catheter is withdrawn, as illustrated by FIG. 3. Due to the formation of the stent from an elongated tubular member, the straight and undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the cylindrical rings closely spaced at regular intervals, provide uniform support for the wall of the artery, and consequently are well adapted to tack up and hold in place small flaps or dissections in the wall of the artery, as illustrated in FIGS. 2 and 3.

Figure 4:
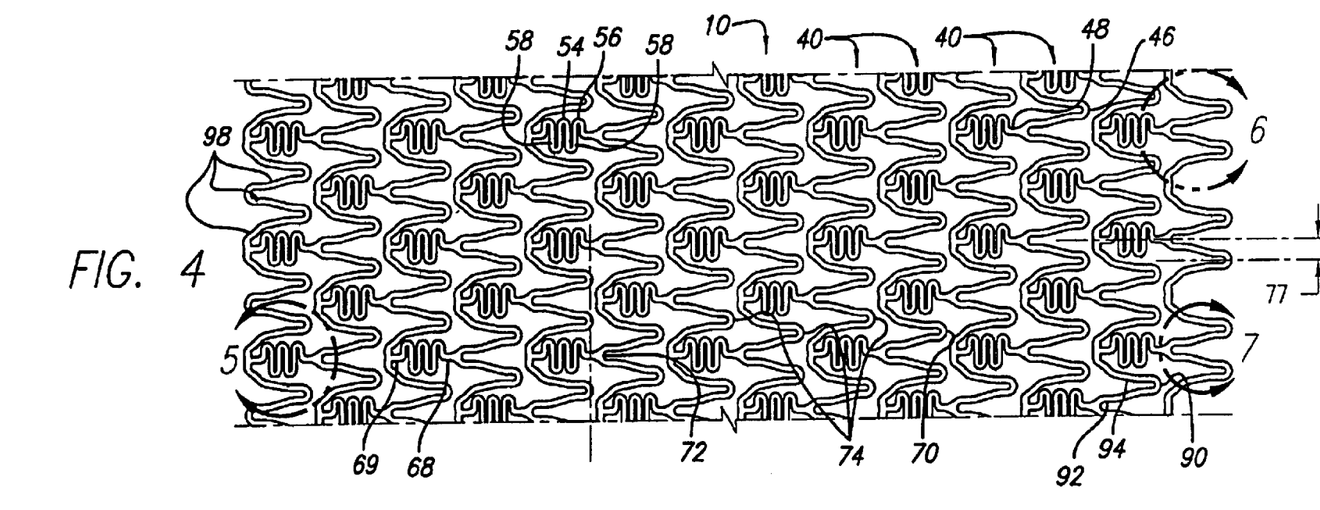
FIG. 4 is a plan view of a flattened stent which illustrates the pattern of the stent shown in FIGS. 1–3.

FIGS. 4–10 depict stent 10 in various configurations. Turning to FIG. 4, stent 10 is shown in a flattened condition so that the pattern can be clearly viewed, even though the stent is never in this form. The stent is typically formed from a tubular member, however, it can be formed from a flat sheet such as shown in FIG. 4 and rolled into a cylindrical configuration.

Figure 6:
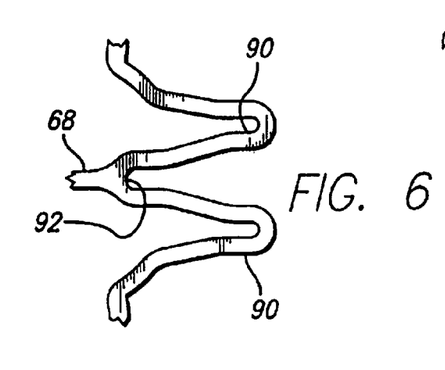
FIG. 6 is an enlarged sectional view of FIG. 4 depicting several peaks of a cylindrical ring.
Figure 7:
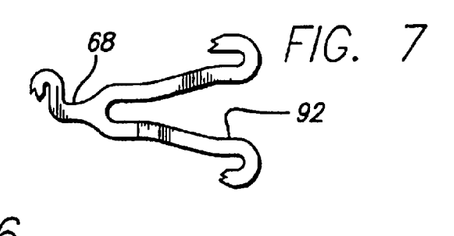
FIG. 7 is an enlarged sectional view of FIG. 4 depicting a Y-shaped portion of the cylindrical ring.
Figure 8A:
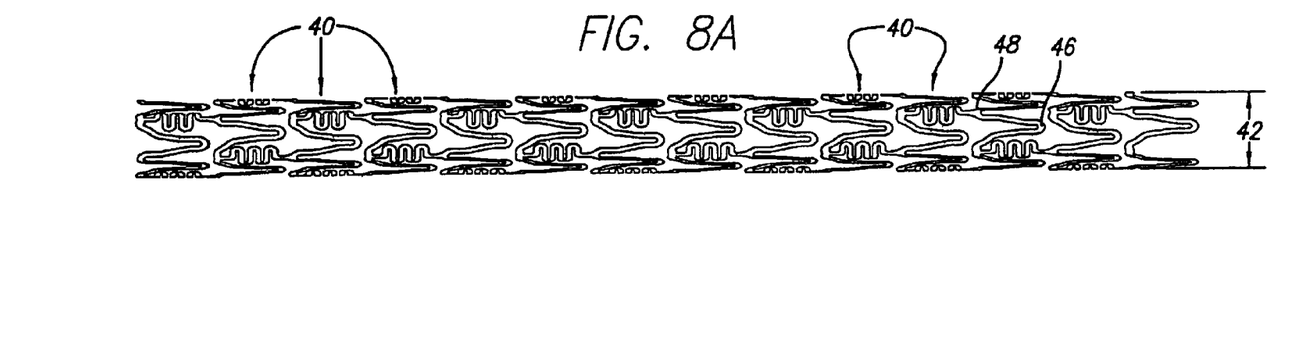
FIG. 8A is a side view of a stent in an unexpanded state.
Figure 9:
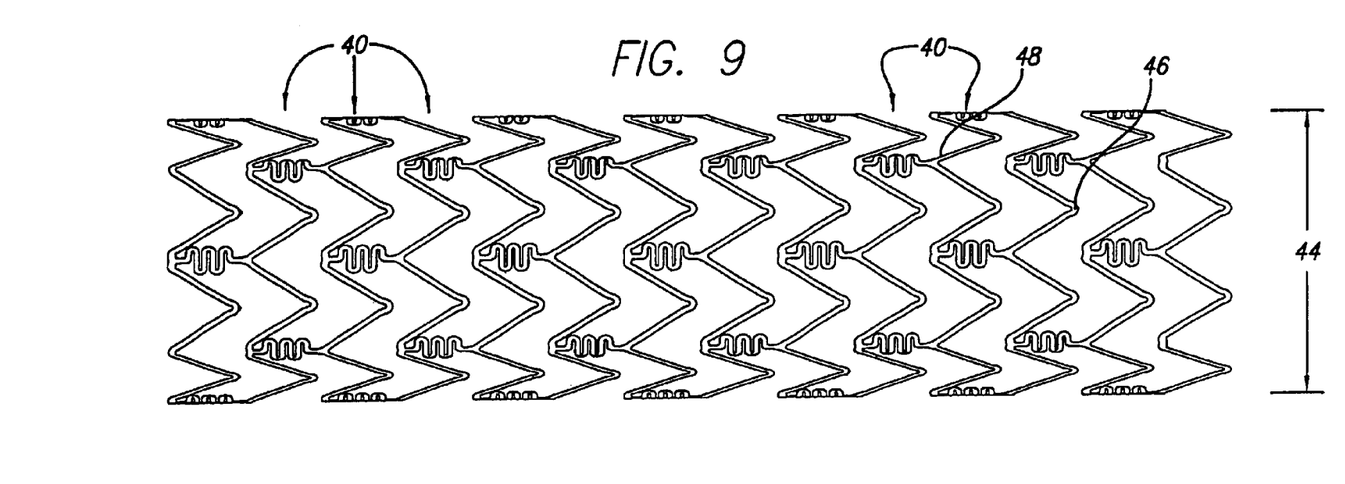
FIG. 9 is a perspective view of the stent of FIG. 8A in an expanded condition.

As shown in FIGS. 4–7, stent 10 is made up of a plurality of cylindrical rings 40 which extend circumferentially around the stent when it is in a tubular form (see FIG. 8). The stent has a delivery diameter 42 as shown in FIG. 8, and an implanted diameter 44 as shown in FIG. 9. Each cylindrical ring 40 has a cylindrical ring proximal end 46 and a cylindrical ring distal end 48. Typically, since the stent is laser cut from a solid tube there are no discreet parts such as the described cylindrical rings. However, it is beneficial for identification and reference to various parts to refer to the cylindrical rings and the following parts of the stent.

Each cylindrical ring 40 defines a cylindrical plane 50 which is a plane defined by the proximal and distal ends 46, 48 and the circumferential extent as the cylindrical ring travels around the cylinder. Each cylindrical ring includes cylindrical outer wall surface 52 which defines the outermost surface of the stent, and cylindrical inner wall surface 53 which defines the innermost surface of the stent. Cylindrical plane 50 follows the cylindrical outer wall surface.

In keeping with the invention, undulating link 54 is positioned within cylindrical plane 50. The undulating links connect one cylindrical ring to an adjacent cylindrical ring and provide overall longitudinal flexibility to the stent due to their unique construction. The flexibility of undulating links derives in part from bends 56 connected to straight portions 58 wherein the straight portions are substantially perpendicular to the longitudinal axis of the stent. Thus, as the stent is being delivered through a tortuous vessel, such as a coronary artery, the bends 56 and straight portions 58 of the undulating links will permit the stent to flex in the longitudinal direction which substantially enhances delivery of the stent to the target site. The number of bends and straight portions can be increased or decreased from that shown, to achieve differing flexibility constructions. With the straight portions being substantially perpendicular to the stent longitudinal axis, the undulating link acts like a hinge to provide flexibility. A straight link that is parallel to the stent axis typically is not flexible and does not add to the flexibility of the stent.

Cylindrical rings 40 can be nested such that adjacent rings slightly overlap in the longitudinal direction so that one ring is slightly nested within the next ring and so on. The degree of nesting is dictated primarily by the length of each cylindrical ring, the number of undulations in the rings, the thickness of the struts that make up the rings, and the radius of curvature, all in conjunction with the crimped or delivery diameter of the stent. If the rings are substantially nested one within the other, it may be difficult to crimp the stent to an appropriate delivery diameter without the various struts overlapping. It is also contemplated that the rings are slightly nested even after the stent is expanded, which enhances vessel wall coverage. In some circumstances, it may not be desirable to nest one ring within the other, which is also contemplated by the invention.

Figure 5:
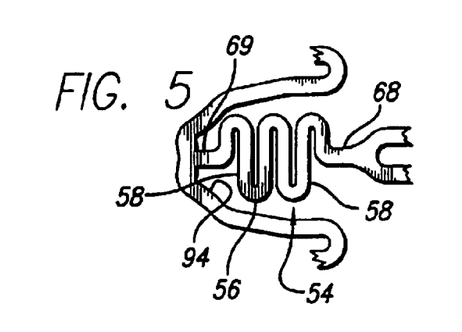
FIG. 5 is an enlarged view of a portion of the stent shown in FIG. 4 depicting an undulating link connecting portions of adjacent cylindrical rings.

Referring to FIGS. 5–7, the stent of the invention can be described as having cylindrical rings formed of U-shaped portions 90, Y-shaped portions 92, and W-shaped portions 94. Again, while the stent is generally laser cut from a solid tube and it typically has no discreet parts, for ease of identification the stent of the invention also can be referred to as having U-, Y-, and W-shaped portions. The U-shaped portions have no supporting structure attached thereto. The Y-shaped portions, at their base, or apex, have arm 68 extending therefrom and attached to undulating link 54. The W portion has at its base or curve portion arm 69 which attaches at the other end of the undulating link. The length of the arms attaching the links to the rings can vary. Importantly, the arms should be sized in conjunction with the undulating link so that the link is properly positioned in the W-shaped portion. Preferably, undulating link 54 is contained within W-shaped portion 94, which should be wide enough to accommodate the undulating link when the stent is crimped so that no portion of the undulating link and the W-portion overlap. Preferably, the undulating link and the W-shaped portion are in the same cylindrical plane 50 as defined by the cylindrical outer wall surface 52 and the cylindrical inner wall surface 53.

Referring to FIGS. 5–7, the stent of the invention can be described as having cylindrical rings formed of U-shaped portions 90, Y-shaped portions 92, and W-shaped portions 94. Again, while the stent is generally laser cut from a solid tube and it typically has no discreet parts, for ease of identification the stent of the invention also can be referred to as having U-, Y-, and W-shaped portions. The U-shaped portions have not supporting structure attached thereto. The Y-shaped portions, at their base, or apex, have arm 68 extending therefrom and attached to undulating link 54. The W portion has at its base or curve portion arm 69 which attaches at the other end of the undulating link. The length of the arms attaching the links to the rings can vary. Importantly, the arms should be sized in conjunction with the undulating link so that the link is properly positioned in the W-shaped portion. Preferably, undulating link 54 is contained within W-shaped portion 94, which should be wide enough to accommodate the undulating link when the stent is crimped so that no portion of the undulating link and the W-portion overlap. Preferably, the undulating link and the W-shaped portion are in the same cylindrical plane 50 as defined by the cylindrical outer wall surface 52 and the cylindrical inner wall surface 53.

Figures 8B, 10, 11, 12:
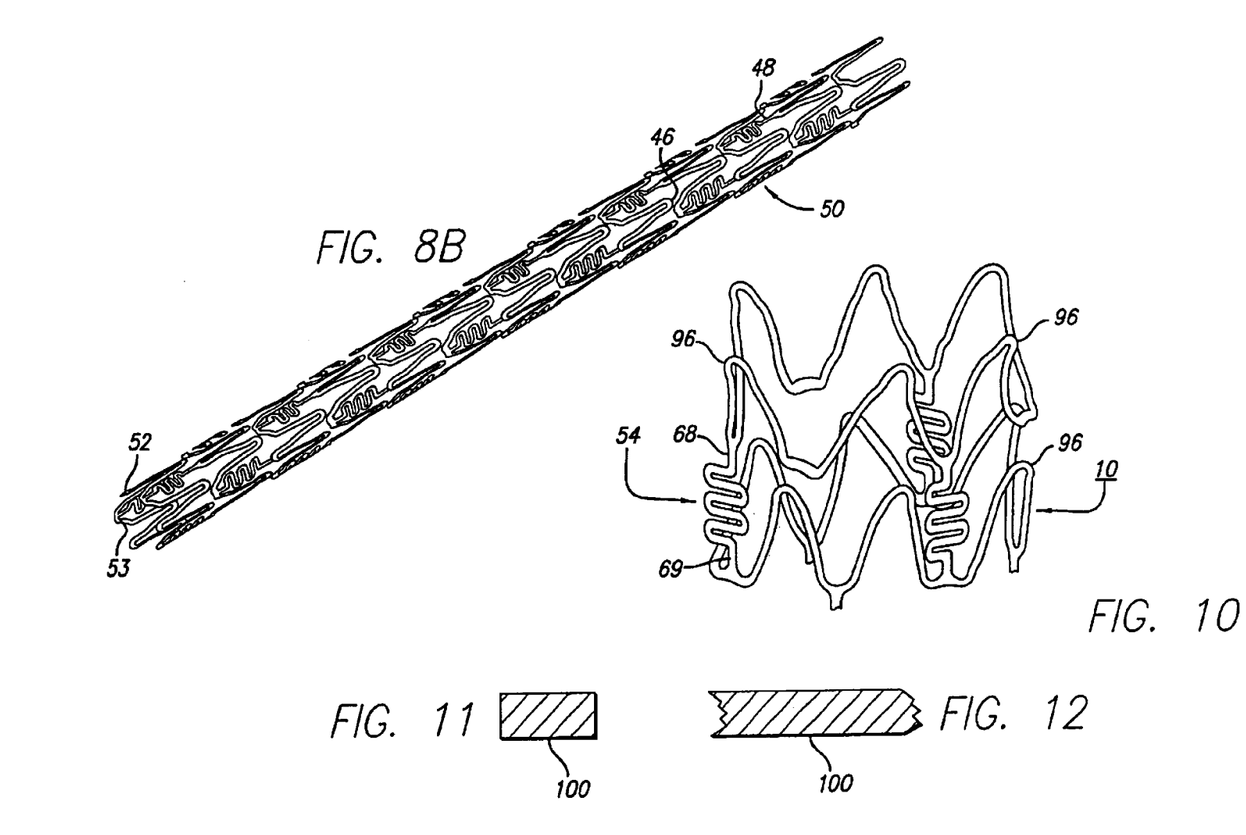
FIG. 8B is a perspective view of the stent of FIG. 8A depicting the cylindrical wall defined by each cylindrical ring.
FIG. 10 is a perspective view of the stent of FIG. 9 depicting projecting edges that project radially outwardly from the cylindrical wall.
FIG. 11 is a cross-sectional view of the stent strut.
FIG. 12 is a cross-sectional view of a wider stent strut.

As shown in FIG. 10, under certain stent configurations portions of the stent may project radially outwardly when the stent is expanded from its delivery diameter where it is crimped on the balloon to its expanded diameter when it is implanted in the vessel or artery. For example, as shown in FIGS. 4, 11 and 12, when a strut 98 (in any section of the stent) has an equal width and thickness, projecting edges 96 likely will form when the stent is expanded from its delivery diameter to its implanted diameter. Typically, however, no projecting edges will form when a variable thickness strut is used, that is when the strut is radially thinner than it is wide. Thus, when a rectangular strut 100 forms the stent, as shown in FIGS. 11 and 12, it is expected that no projecting edges will form upon expansion for this particular stent pattern.

Figure 13:
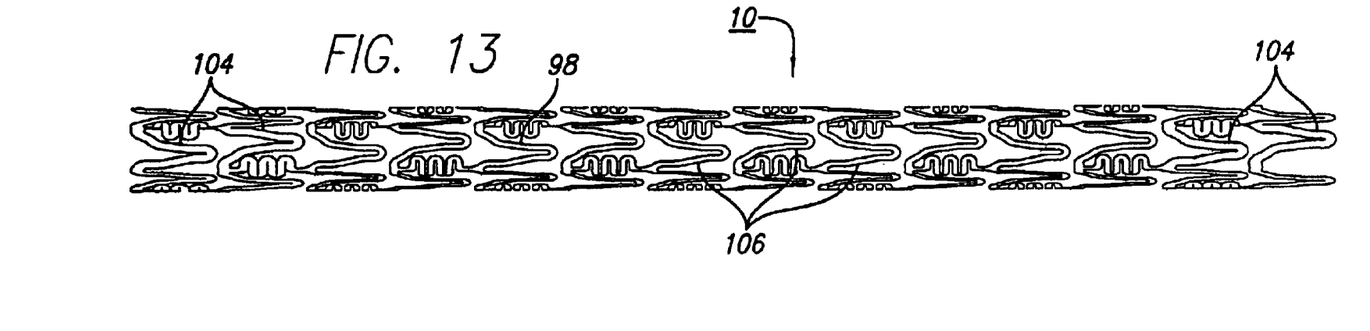
FIG. 13 is a side view of the stent depicting cylindrical rings at the end of the stent having a thicker radial cross-section than the rings at the center of the stent.

In one aspect of the invention, the stent is formed so that the struts 98 (FIG. 13) have variable thickness (not shown) along the stent length. As one example, it is contemplated that struts 104 at the ends of the stent may be radially thicker than the struts 106 in the center of the stent for purposes for radiopacity and to counter balloon expansion. When the balloon first inflates, the balloon ends have a tendency to inflate at a faster rate than the balloon center, however, with thicker struts at the stent ends the balloon, and hence the stent, will expand more uniformly.

Figure 14:
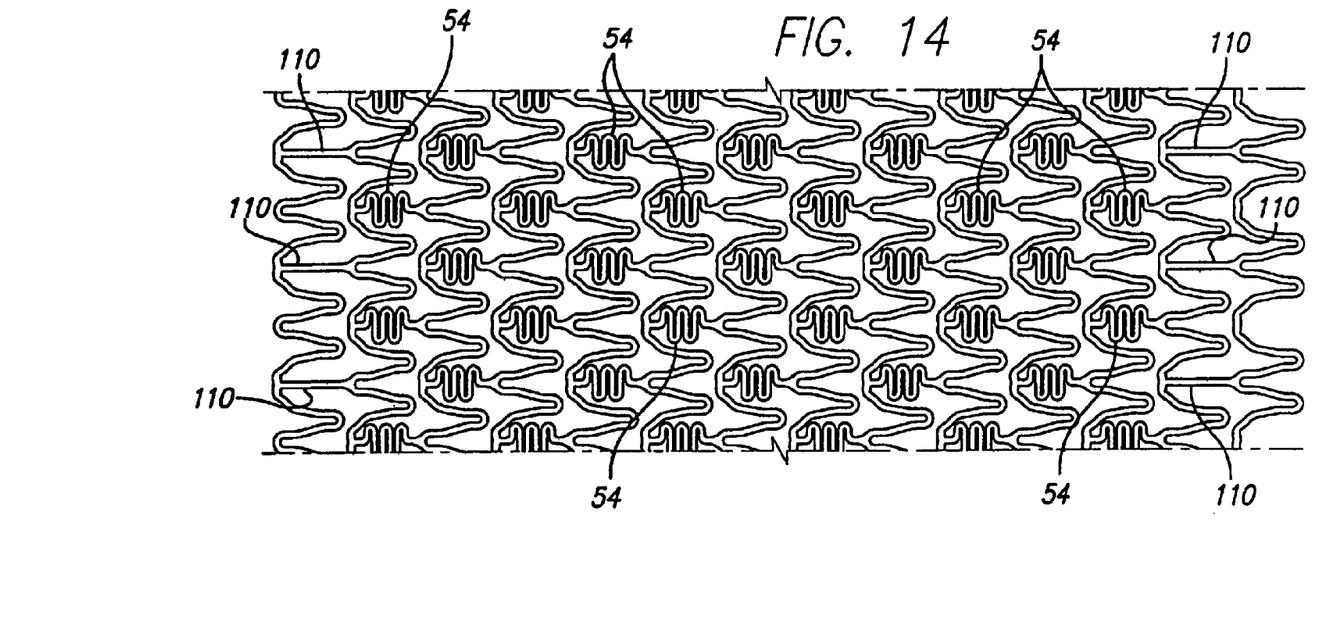
FIG. 14 is a plan view of a flattened stent illustrating a combination of undulating links and straight links.

As described above, it is also contemplated that more or fewer undulating links 54 will be positioned between adjacent cylindrical rings 40. It is also contemplated, in order to increase stent stability, that straight links 110, as shown in FIG. 14, in addition to undulating links 54, connect adjacent cylindrical rings. The straight links will provide stability and assist in preventing stent foreshortening, as do the undulating links. Further, the straight links may provide more rigidity in a localized area, such as at the stent ends, such that it may be desirable to incorporate more straight links between the cylindrical rings at the stent ends, than in the center of the stent.

Figures 15, 16:
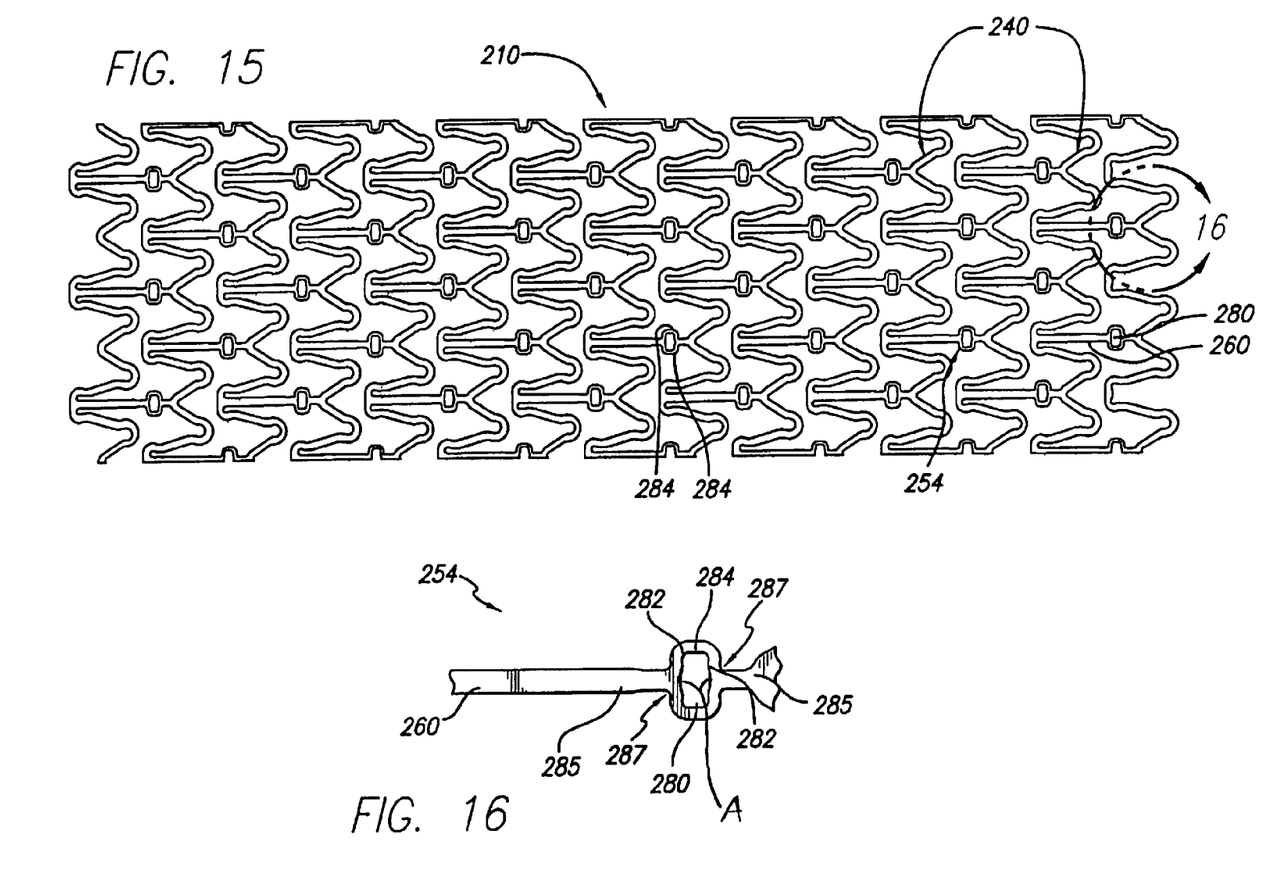
FIG. 15 is a plan view of a flattened stent with a generally rectangular aperture disposed in the straight links and between the cylindrical rings.
FIG. 16 is a detailed plan view of a single straight link with a generally rectangular aperture.

FIGS. 15 and 16 depict another type of link that provides improved stent flexibility in tortuous vessels. A side view of stent 210 depicts cylindrical rings 240 connected by links 254. In one embodiment, link 254 has a straight portion 260 that is generally parallel to the stent's longitudinal axis and a generally rectangular aperture 280 bounded on all sides. Link portions 282 define two sides of rectangular aperture 280 and are generally perpendicular to the stent's longitudinal axis. Link portions 284 connect the link portions 282. Tapered link portions 285 are connected to perpendicular link portions 282 at radii 287.

The increase in stent flexibility created by aperture 280 and the surrounding structure is easily understood. As a stent passes through a curved vessel, half the stent is in tension at the widest part of the curve, and the other half of the stent is in compression, at the narrowest part of the curve. Thus, one half of the stent wants to expand, and the other half wants to contract and the link aperture permits either. In expansion, points A (FIG. 16) move away form each other, while in contraction they move toward each other. As those in the art will appreciate, less force is required to deform the structure bounding aperture 280 than would be necessary to elongate or compress a link if were a straight structure like link portion 260.

Figure 17:
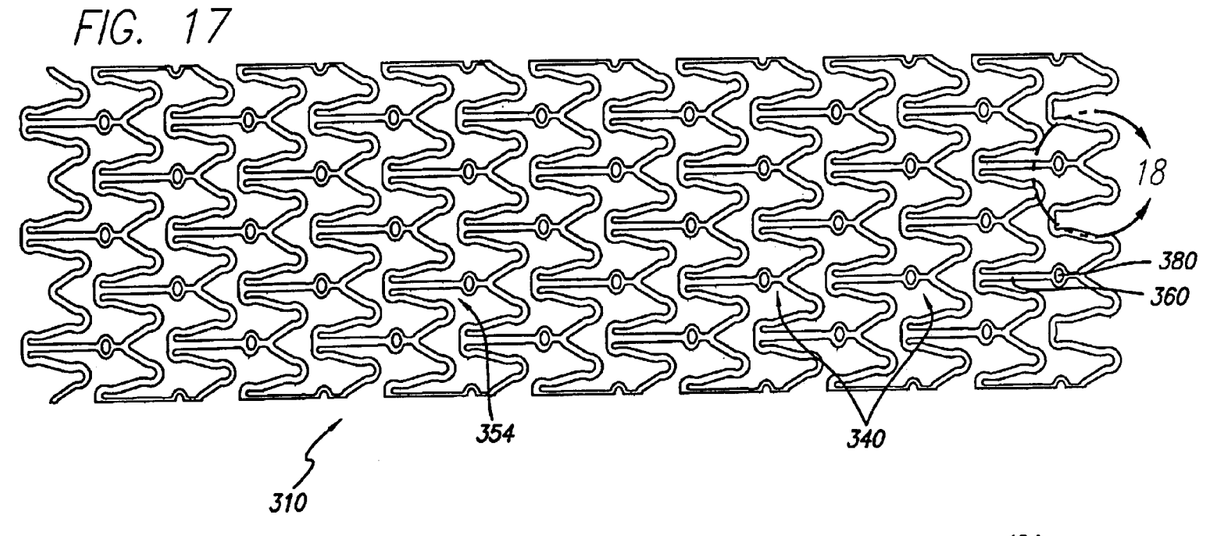
FIG. 17 is a plan view of a flattened stent with an oval aperture disposed in the straight links and between the cylindrical rings.
Figure 18:
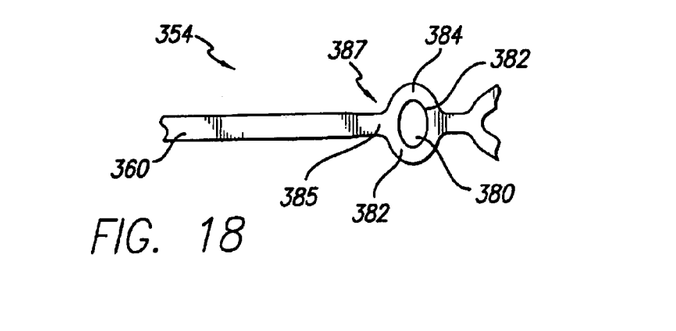
FIG. 18 is a detailed plan view of a single straight link with an oval aperture.

FIGS. 17 and 18 are conceptually similar to FIGS. 15 and 16. The stent 310 comprises a plurality of cylindrical rings 340 connected by links 354. Apertures 380 are elliptically shaped with the major axis of the ellipse running perpendicular to the stent's longitudinal axis. In other words, the long part of the ellipse 382 is perpendicular to the longitudinal axis, and the short elliptical part 384 is parallel. The link 354 also includes tapered portion 385 and radius portion 387. The structural portion surrounding the elliptical aperture 380 responds to stress in much the same way as the rectangular structure in FIG. 16. As the ellipse is stretched in tension it becomes more circular and less elliptical. As the ellipse is placed in compression, it becomes more elliptical, approaching the shape of a thin rectangle, a slit, or even two separate rounded apertures. separated by a contact point.

In the one embodiment of the flexible link with an elliptical aperture, the major and minor axis of the ellipse are parallel and perpendicular to the longitudinal axis of the stent. Thus, in a general sense, the ellipse can be thought of as similar to a rectangle to the extent it has two long sides and two short sides. Preferably, the long sides, i.e., the major axis of the ellipse, are transverse to the longitudinal axis of the stent.

Figure 19:
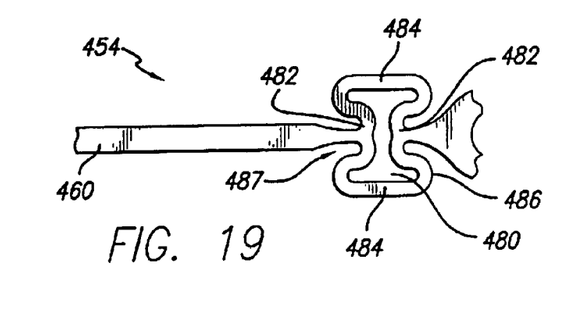
FIG. 19 is a detailed plan view of a single straight link with a generally dog bone shaped aperture.

FIG. 19 depicts a link 454 with a dumbbell or dog bone shaped aperture. 480. Straight portion 460 of link 454 intersects transverse portion 482. The aperture 480 is bounded by transverse and parallel portions 482 and 484 and four curved portions 486. As tension is applied to link 454, radius portions 487 and curved portions 486 tend to straighten as distance between transverse portions 482 increases. When the link 454 is compressed, transverse portions 482 will approach each other to the point of touching.

As one of ordinary skill in the art will appreciate, the flexibility of links 254, 354, and 454 can be controlled by the dimensions of various portions of the links, such as tapering straight portions such as 460, where it meets transverse portion 482. One could also, separately or in combination with the taper, vary radius portion 487 or modify the widths of various structural elements, such as portions 460, 482, 484 or 486.

Other embodiments of the invention, although not shown, are easily developed. For example, on could create a straight link with two differently shaped apertures. Alternatively, one could combine an undulating link with an aperture. The advantage of the present invention resides primarily in having a portion or portions of the connecting link disposed transverse to the stent's longitudinal axis. Thus, whether the link is in tension, compression, or bending, the transverse portion of the link creates greater leverage and thus greater stress on the link, allowing it to flex more easily than other stents.

In one important aspect of the invention, after stent 10 is implanted in a coronary artery, or other vessel, because of its novel design, the cylindrical rings 40 have the ability to flex radially as the vessel pulsates when blood pumps through it. Likewise, because of the novel and unique design of undulating links 54, as the vessel moves and pulsates from the pumping blood, the stent can flex longitudinally. The radial and longitudinal flexing of the stent reduces the likelihood that the stent will cause injury to the intima of a coronary artery, which also may have a tendency to reduce the likelihood of restenosis.

The stent 10 of the present invention can be made in many ways. One method of making the stent is to cut a thin-walled tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art. approaching the shape of a thin rectangle, a slit, or even two separate rounded apertures. separated by a contact point.

The tubing may be made of suitable biocompatible material such as stainless steel or another metal alloy. The stainless steel tube may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch (1.524 mm) in the unexpanded condition, the same outer diameter of the tubing from which it is made, and can be expanded to an outer diameter of 0.1 inch (2.54 mm) or more. The wall thickness of the tubing is about 0.003 inch (0.0762 mm).

The tubing is mounted in a rotatable collet fixture of a machine-controlled apparatus for positioning the tubing relative to a laser. According to machine-encoded instructions, the tubing is rotated and moved longitudinally relative to the laser which is also machine controlled. The laser selectively removes the material from the tubing by ablation and a pattern is cut into the tube. The tube is therefore cut into the discrete pattern of the finished stent.

The process of cutting a pattern for the stent into the tubing is automated except for loading and unloading the length of tubing. In one example, a CNC-opposing collet fixture 22 for axial rotation of the length of tubing is used in conjunction with a CNC X/Y table 25 to move the length of tubing axially relatively to a machine-controlled laser. The entire space between collets can be patterned using the $CO_2$ laser set-up of the foregoing example. The program for control of the apparatus is dependent on the particular configuration used and the pattern to be ablated in the coating.

Cutting a fine structure (0.0035 inches or 0.0889 mm web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes are made typically of stainless steel with an outside diameter of 0.060 to 0.066 inches (1.524–1.676 mm) and a wall thickness of 0.002 to 0.004 inches (0.0508–0.1016 mm). These tubes are fixtured under a laser and positioned utilizing CNC equipment to generate a very intricate and precise pattern. Due to the thin wall and the small geometry of the stent pattern (0.0035 inches or 0.0889 mm typical web width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris free cut, a Q-switched Nd-YAG, typically available from Quantronix of Hauppauge, N.Y., that is frequency doubled to produce a green beam at 532 nanometers is utilized. Q-switching produces very short pulses (<100 nS) of high peak powers (kilowatts), low energy per pulse ($\leq$3 mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up to stent structure. Hence, the system of the present invention makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle (0.018 inches or 0.4572 mm I.D.) is centered around the focused beam with approximately 0.010 inches (0.254 mm) between the tip of the nozzle and the tubing. The jet is pressurized with oxygen at 20 psi and is directed at the tube with the focused laser beam exiting the tip of the nozzle (0.018 inches or 0.4572 mm dia.). The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube I.D., a stainless steel mandrel (approx. 0.034 inches or 0.8636 mm dia.) is placed inside the tube and is allowed to roll on the bottom of the tube as the pattern is cut. This acts as a beam/debris block protecting the far wall I.D.

Alternatively, this may be accomplished by inserting a second tube inside the stent tube which has an opening to trap the excess energy in the beam which is transmitted through the kerf along which collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005 inches or 0.0127 mm) with the molten slag re-solidifying along the cut. This traps the cut out scrap of the pattern requiring further processing. In order to remove the slag debris from the cut allowing the scrap to be removed from the remaining stent pattern, it is necessary to soak the cut tube in a solution of HCL for approximately 8 minutes at a temperature of approximately 55° C. (131° F.). Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCL for 1–4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structure are rinsed in water. They are now ready for electropolishing.

The stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110°–135° F. (43°–57° C.). and the current density is about 0.4 to about 1.5 amps per in.$^2$. Cathode to anode area should be at least about two to one. The stents may be further treated if desired, for example by applying a biocompatible coating.

It will be apparent that both focused laser spot size and depth of focus can be controlled by selecting beam diameter and focal length for the focusing lens. It will be apparent that increasing laser beam diameter, or reducing lens focal length, reduces spot size at the cost of depth of field.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal. As depicted, cylindrical rings 40 are comprised of struts 98 which have generally rectangular cross-sections 100 when the stent is laser S cut from a tubular member. The struts have generally perpendicular edges formed by the laser cut. The resulting stent structure provides superior performance.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory or superelastic alloys. Shape memory alloys are well known and include, but are not limited to titanium, tantalum, nickel titanium and nickel/titanium/vanadium. Any of the superelastic or shape memory alloys can be formed into a tube and laser cut in order to form the pattern of the stent of the present invention. As is well known, the superelastic or shape memory alloys of the stent of the present invention can include the type known as thermoplastic martensitic transformation, or display stress-induced martensite. These types of alloys are well known in the art and need not be further described here.

Importantly, a stent formed of shape memory or superelastic alloys, whether the thermoelastic or the stress-induced martensite-type, can be delivered using a balloon catheter of the type described herein, or in the case of stress induced martensite, be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of crowns per ring, materials used, and the like have been described herein and are provided as examples only. Other modifications and improvements may be made without departing from the scope of the invention.

What is claimed:

1. A flexible intravascular stent for use in a body lumen, comprising:

a plurality of cylindrical rings interconnected to form the stent and a stent longitudinal axis, each cylindrical ring having a first delivery diameter and a second implanted diameter;

each cylindrical ring having a plurality of peaks and valleys and a proximal end and a distal end defining a cylindrical wall extending circumferentially between the proximal end and the distal end of the cylindrical ring; and at least one flexible link attaching each cylindrical ring to an adjacent cylindrical ring, the link including a first link portion connected to only one ring and a second link portion connected only to the adjacent ring, and a completely bounded aperture disposed between the first and second link portions and disposed nearer one of the adjacent rings, with the bounded aperture having a major axis and a minor axis, with the major axis disposed generally transverse to the stent longitudinal axis.

2. The stent of claim 1, wherein the bounded aperture comprises two aperture defining portions generally perpendicular to the stent longitudinal axis.

3. The stent of claim 2, wherein the bounded aperture comprises an ellipse.

4. The stent of claim 2, wherein the bounded aperture is in the shape of a dog bone.

5. The stent of claim 2, wherein the bounded aperture is generally rectangular.

6. The stent of claim 2, further comprising an undulating link.

7. The stent of claim 6, wherein the undulating link comprises at least one bend connected to a substantially straight portion disposed generally perpendicular to the stent longitudinal axis.

8. The stent of claim 7, wherein the undulating link is positioned substantially within the cylindrical wall of the cylindrical ring.

9. The stent of claim 2, wherein each cylindrical ring comprises peaks and valleys in phase with the peaks and valleys of an adjacent cylindrical ring.

10. The stent of claim 1, further comprising at least one tapered link portion connecting the link to the aperture portion.

11. The stent of claim 10, further comprising a radiused link portion, connecting the tapered link portion to the aperture link portion.

12. The stent of claim 1, wherein the stent is formed from stainless steel.

13. The stent of claim 1, wherein the stent is formed from a shape memory alloy.

14. The stent of claim 1, wherein the stent is formed from a pseudo elastic metal alloy.

15. The stent of claim 1, wherein the first and second link portions are parallel to the stent's longitudinal axis.

16. The stent of claim 1, wherein the at least one aperture defining portion includes a width that is narrower than the width of the first and second link portions.

17. A flexible intravascular stent for use in a body lumen, comprising:

a plurality of cylindrical rings interconnected to form the stent and a stent longitudinal axis, each cylindrical ring having a first delivery diameter and a second expanded diameter, each cylindrical ring having a plurality of peaks and valleys defining ends of the rings; and at least one link attaching each cylindrical ring to an adjacent cylindrical ring, the link including (1) a first link portion connected only to one ring and a second link portion connected only to the adjacent ring, (2) a completely bounded aperture disposed in the link between the first and second link portions and also disposed nearer one of the ends of the adjacent rings, (3) a major axis of the bounded aperture disposed generally perpendicular to the stent longitudinal axis, and (4) a tapered link portion connecting the link to the generally perpendicular link portion.

18. The stent of claim 17, wherein the link further comprises a radiused portion connecting the tapered portion and the perpendicular portion.

19. The stent of claim 18, wherein the aperture is shaped as one of a) an oval, b) a dog bone, or c) a rectangle.

20. The stent of claim 18, further comprising an undulating link portion with at least one substantially straight portion disposed generally perpendicular the stent longitudinal axis.

21. The stent of claim 20, wherein the substantially straight portion of the at least one undulating link is perpendicular to the stent longitudinal axis when the stent is in a first delivery diameter configuration and when the stent is in a second expanded diameter configuration.

22. The stent of claim 21, wherein the undulating link comprises a plurality of straight portions disposed generally perpendicular to the stent longitudinal axis.

23. The stent of claim 17, wherein each cylindrical ring comprises peaks and each ring's peaks are in phase with the peaks of the adjacent cylindrical ring.

24. The stent of claim 17, wherein the stent is formed from a tube.

25. The stent of claim 17, wherein the cylindrical rings are defined by a plurality of struts, wherein at least one of the struts has a varying cross section.

26. The stent of claim 17, wherein the first and second link portions are parallel to the stent's longitudinal axis.

27. The stent of claim 17, wherein the first and second link portions are parallel to the stent's longitudinal axis.

28. A flexible intravascular stent for use in a body lumen, comprising:

a plurality of cylindrical rings interconnected to form the stent and a stent longitudinal axis, each cylindrical ring having a first delivery diameter, a second expanded diameter, and a plurality of peaks and valleys; and at least one link attaching each cylindrical ring to an adjacent cylindrical ring, the link including (1) a first link portion connected only to one ring and a second link portion connected only to the adjacent ring, (2) a completely bounded aperture disposed in the link between the first and second link portions, the aperture including a major axis disposed generally perpendicular to the stent longitudinal axis, (3) a tapered portion connecting the link to the generally perpendicular portion, (4) a radiused portion connecting the tapered and perpendicular portions, and (5) at least two undulating link portions, one undulating link portion being disposed between the aperture and one ring, and another undulating link being disposed between the aperture and an adjacent ring.

29. A flexible intravascular stent for use in a body lumen, comprising:

a plurality of cylindrical rings interconnected to form the stent with a longitudinal axis, each cylindrical ring having a first delivery diameter and a second expanded diameter;

the cylindrical rings having a plurality of U shaped portions, Y shaped portions, and W shaped portions that are expandable;

each cylindrical ring having a proximal end and a distal end defining a cylindrical wall extending circumferentially between the proximal end and the distal end of the cylindrical ring; and at least one flexible link attaching each cylindrical ring to an adjacent cylindrical ring, the link including a first link portion connected only to one ring and a second link portion connected only to the adjacent ring, and a completely bounded aperture disposed between the first and second link portions ends of the adjacent cylindrical rings, the aperture being defined in part by two aperture defining link portions, which form a major axis of the aperture that is disposed generally perpendicular to the stent longitudinal axis and being connected to the link by two tapered and radiused link portions disposed on opposite sides of the aperture.

30. The stent of claim 29, wherein the aperture is configured in one of a generally rectangular, oval, or dog bone shape.

31. The stent of claim 30, further comprising undulating links with a plurality of bends.

32. The stent of claim 30, wherein the stent is formed from a tube.

33. The stent of claim 30, wherein the Y shaped portions are formed from the combination of the U shaped portions with the undulating links.

34. The stent of claim 30, wherein the W shaped portions incorporate at least a portion of the undulating links.

35. The stent of claim 29, wherein the cylindrical rings are defined by a plurality of struts, wherein at least one of the struts has a varying cross section.

36. The stent of claim 35, wherein at least some of the struts have a variable thickness in the radial direction.

* * * * *

UNITED STATES PATENT AND TRADEMARK OFFICE
CERTIFICATE OF CORRECTION

PATENT NO. : 6,929,660 B1
DATED : August 16, 2005
INVENTOR(S) : Stephen D. Ainsworth and E. Tina Cheng It is certified that error appears in the above-identified patent and that said Letters Patent is hereby corrected as shown below:

Column 3,
Line 20, delete "tent" and insert -- stent --.

Column 4,
Line 51, delete "in." and insert -- in --.

Column 5,
Line 63, insert new paragraph
--Referring to FIGS. 4-9, the stent 10 can be described more particularly as having a plurality of peaks 70 and valleys 72. Although the stent is not divided into separate elements, for case of discussion references to peaks and valleys is appropriate. The number of peaks and valleys, sometimes referred to as crowns, can vary in number for each ring depending upon the application. Thus, for example, if the stent is to be implanted in a coronary artery, a lesser number of peaks and valleys (or crowns) are required than if the stent is implanted in a peripheral artery, which has a larger diameter than a coronary artery. As can be seen in FIG. 4, peaks 70 are in phase 74, meaning that the peaks 70 are substantially aligned along the longitudinal axis of the stent. It may be desirable under certain circumstances to position peaks 70 so that they are out of phase (not shown), that is, the peaks of one ring would be circumferentially offset 77 from the valleys and from the undulating link 54. Positioning the peaks, valleys, and undulating links in this manner provides a stent having uniform expansion capabilities, high radial strength, a high degree of flexibility, and sufficient wall coverage to support the vessel.--.

Column 6,
Delete lines 18-39.

Column 7,
Line 42, delete "apertures." and insert -- apertures --.
Line 52, delete "aperture." and insert -- aperture --.

Column 8,
Line 30, delete "approaching the shape of a thin rectangle, a slit, or even two separate rounded apertures. Separated by a contact point.".

UNITED STATES PATENT AND TRADEMARK OFFICE
CERTIFICATE OF CORRECTION

PATENT NO.    : 6,929,660 B1
DATED         : August 16, 2005
INVENTOR(S)   : Stephen D. Ainsworth and E. Tina Cheng It is certified that error appears in the above-identified patent and that said Letters Patent is hereby corrected as shown below:

Column 11,
Line 25, delete "laser S" and insert -- laser --.

Signed and Sealed this

Twenty-eighth Day of February, 2006

JON W. DUDAS
*Director of the United States Patent and Trademark Office*